US00PP11019P

United States Patent [19]

Evers

[11] Patent Number: Plant 11,019

[45] Date of Patent: Aug. 3, 1999

[54] HYBRID TEA ROSE PLANT NAMED 'TANSELMI'

[75] Inventor: Hans-Jürgen Evers, Uetersen, Germany

[73] Assignee: Bear Creek Gardens, Inc., Medford, Oreg.

[21] Appl. No.: 09/016,018

[22] Filed: Jan. 30, 1998

[51] Int. Cl.[6] ..... A01H 5/00

[52] U.S. Cl. ..... Plt./138

[58] Field of Search ..... Plt./137, 138, 139, Plt./130

*Primary Examiner*—Howard J. Locker

*Attorney, Agent, or Firm*—Klarquist Sparkman Campbell Leigh & Whinston, LLP

[57] ABSTRACT

Hybrid tea rose plant having blossoms of a dark pink color on long stems having long life both on the plant and as a cut flower.

1 Drawing Sheet

The present invention relates to a new and distinct variety of rose plant of the hybrid tea class which was originated by me by discovering in a greenhouse in Uetersen, Germany a spontaneous flower color mutation of the variety 'TANselbon' (unpatented).

'TANselmi' is a stable and novel flower color mutation of 'TANselbon'. The flowers of 'TANselmi' are of a dark pink color while the flowers of 'TANselbon' are of a light pink color. 'TANselmi' has a very similar vase life (twelve to fourteen days), production of cut flower stems (160–180 per square meter), and stem length (22–26 inches) as 'TANselbon'. 'TANselmi' distinguishes from its parent essentially only in its flower color.

Asexual reproduction of this new variety by budding, as performed at Uetersen, Germany and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Parent*.—Mutant of 'TANselbon' (unpatented).

Classification:

*Botanical*.—Rosa hybrida.

*Commercial*.—Hybrid Tea.

FLOWER

Observations made from specimens grown in a greenhouse environment at Uetersen, Germany and at Somis, Calif. from January, 1997 to January, 1998.

Blooming habit: Continuous.

Bud:

*Size*.—One and three-quarter inches long when the petals start to unfurl.

*Form*.—The bud form is long, pointed ovoid.

*Color*.—When sepals first divide, bud color is Red-Purple Group 58D. When half blown, the upper sides of the petals are Red Group 54B; and the lower sides of the petals are Red-Purple Group 58D.

*Sepals*.—Color: Green group 138B. Surface texture: Covered in fine hairs. There are three lightly appendaged sepals. There are two unappendaged sepals with hairy edges.

*Receptacle*.—Color: Yellow-Green Group 146C. Shape: Funnel. Size: Large (7/16"×3/8"). Surface: Smooth.

*Peduncle*.—Length: Medium (3½"). Surface: Smooth. Color: Medium green. Strength: Stiff, erect.

Bloom:

*Size*.—Large. Average open size is 4 inches.

*Borne*.—Singly.

*Stems*.—Long (22–26"), strong.

*Form*.—When first open: High centered. Permanence: Retains its form to the end; outer petal edges curl back.

*Petalage*.—Number of petals under normal conditions: 35.

*Color*.—The upper sides of the petals are Red Group 54B. The reverse sides of the petals are Red-Purple Group 58D. The base of each petals has a distinct 7/16"×5/16", white half moon at the point of attachment. The major color on the upper sides is Red Group 54B.

*Variegations*.—Occasional greenish-white streaks on the guard petals.

*Discoloration*.—There is no change through to petal drop both on the plant and in the vase.

*Fragrance*.—Slight.

Petals:

*Texture*.—Thick.

*Shape*.—Round.

*Form*.—Tips slightly recurved.

*Arrangement*.—Imbricated. Petaloids in the center are few.

*Persistence*.—Drop off cleanly before drying.

*Lastingness*.—On the plant: Long (nine to ten days). As a cut flower: Long (twelve to fourteen days).

Reproductive parts:

*Anthers*.—Size: Medium. Quantity: Many. Color: Yellow. Arrangement: Regular around styles.

*Filaments*.—Color. Yellow.

*Pollen*.—Color: Gold yellow.

*Styles*.—Color: Reddish.

*Stigmas*.—Color: Greenish-white.

Plant:

*Form*.—Bush.

*Growth*.—Very vigorous; upright; branching.

*Mature plant*.—Height: Six feet. Width: Four feet.

*Foliage*.—Number of leaflets on normal mid-stem leaves: Five.

*Size*.—Large. (5½"×3½").

*Quantity*.—Abundant.

*Color*.—New foliage: Upper surface: Greyed-Red Group 178B. Lower surface: Greyed-Red Group 178B; both very quickly turning to the green colors of the mature leaf. Old foliage: Upper surface: Green Group 139A. Lower surface: Green Group 139C.

*Shape*.—Broadly oval.

*Texture*.—Upper side: Smooth.

*Edge*.—Serrated.

*Serration*.—Single, small.

*Petiole rachis*.—Color: Green.

*Petiole underside*.—Smooth, with occasional prickles.

*Stipules*.—Medium (½"); serrated, bearded.

*Disease resistance*.—Resistant to mildew under normal growing conditions at Uetersen, Germany and Somis, Calif.

Wood:

*New wood*.—Color: Reddish. Bark: Smooth.

*Old wood*.—Color: Green. Bark: Smooth.

Prickles:

*Quantity*.—On main canes from base: Few. On laterals from main canes: Few.

*Form*.—Medium; straight to hooked downward.

*Color when young*.—Slightly Red.

Small prickles:

*Quantity*.—On main stalks: None. On laterals: None.

I claim:

1. A new and distinct variety of rose plant of the hybrid tea class, substantially as herein shown and described, characterized particularly as to novelty by its blossoms of a dark pink color on long stems having long life both on the plant and as a cut flower.

* * * * *

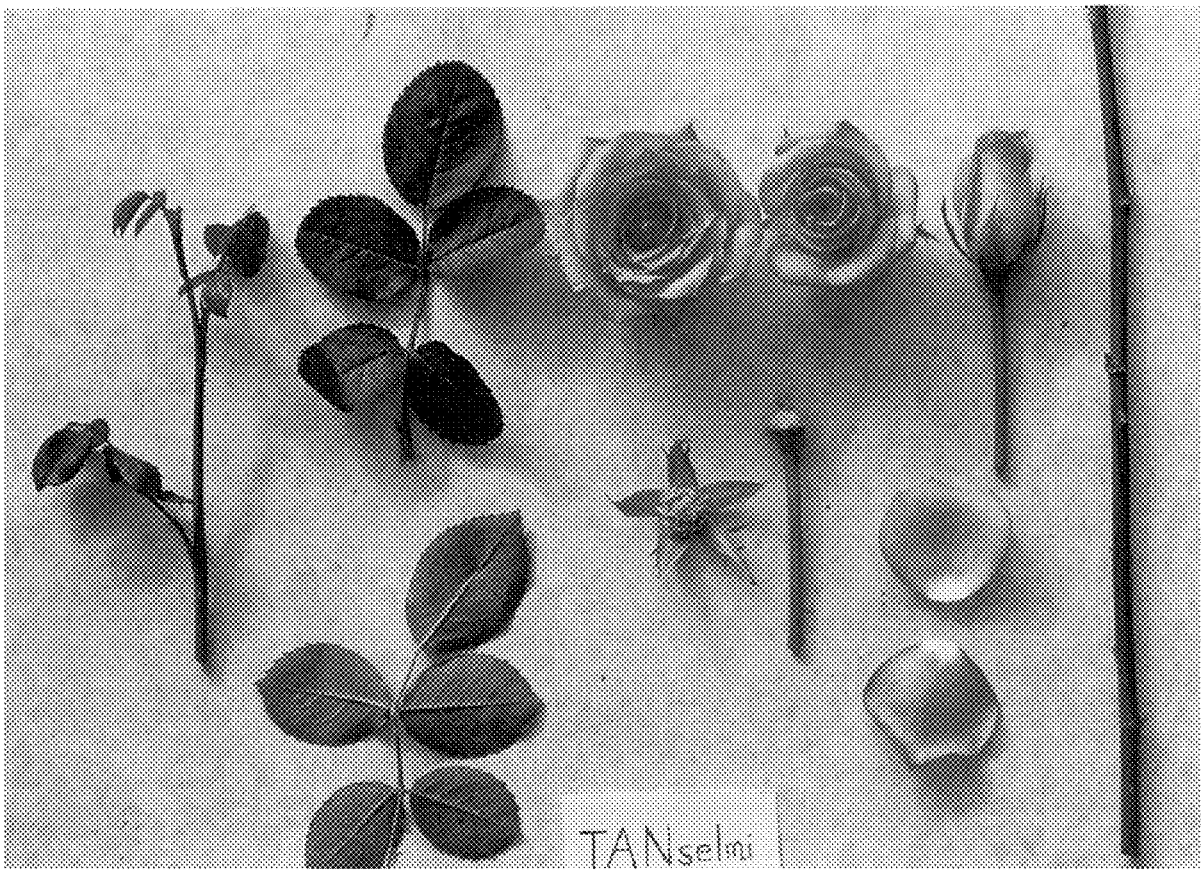
TANselmi